US006625573B2

(12) United States Patent
Petrosov

(10) Patent No.: US 6,625,573 B2
(45) Date of Patent: Sep. 23, 2003

(54) METHOD AND APPARATUS OF MOLECULAR WEIGHT DETERMINATION FOR GASES FLOWING THROUGH THE COMPRESSOR

(76) Inventor: Petr A. Petrosov, 4909 Westbrook Pl., West Des Moines, IA (US) 50266

( * ) Notice: Subject to any disclaimer, the term of this patent is extended or adjusted under 35 U.S.C. 154(b) by 100 days.

(21) Appl. No.: 09/898,764

(22) Filed: Jul. 3, 2001

(65) Prior Publication Data

US 2002/0062679 A1 May 30, 2002

Related U.S. Application Data

(60) Provisional application No. 60/213,233, filed on Jun. 20, 2000.

(51) Int. Cl.[7] .................................................. G06F 7/06
(52) U.S. Cl. ............................. 703/23; 702/24; 702/26; 702/27; 702/30
(58) Field of Search .............................. 702/23, 24, 26, 702/27, 30, 129, 138, 173; 250/306; 700/289; 361/228; 73/23.2; 417/2–6

(56) References Cited

U.S. PATENT DOCUMENTS

| 4,825,300 A | | 4/1989 | Omori ........................ 358/328 |
|---|---|---|---|
| 4,825,380 A | * | 4/1989 | Hobbs ......................... 364/499 |
| 4,999,276 A | | 3/1991 | Kuwabara et al. ........... 430/264 |
| 5,195,875 A | * | 3/1993 | Gaston ........................ 417/282 |
| 5,508,943 A | * | 4/1996 | Batson et al. ........... 364/551.01 |
| 5,743,715 A | * | 4/1998 | Staroselsky et al. ............ 417/6 |

* cited by examiner

*Primary Examiner*—Marc S. Hoff
*Assistant Examiner*—Felix Suarez
(74) *Attorney, Agent, or Firm*—Daniel A. Rosenberg; Kent A. Herink; Davis Brown Law Firm

(57) ABSTRACT

A performance map is provided comprising a plurality of performance curves showing head/flow conditions at various compressor speeds, terminating at one end at surge points. The performance curves are converted into deviation curves representing deviations from the surge point at the head/flow conditions. The curves are merged into a universal compressor curve with a merge-function and a pre-defined tolerance. Imaginary map head/flow values are calculated using the universal compressor curve, merge-function, deviation curves, and performance curves at the compressor speed. A ratio of the imaginary map head/flow values is compared to a ratio of the actual head/flow values at the compressor speed to determine if the ratios are within a pre-defined tolerance. The process repeats until the ratios are within the tolerance. The molecular weight of the compressor gas is calculated using a function of the actual and imaginary flow values and/or head values.

6 Claims, 2 Drawing Sheets

METHOD AND APPARATUS OF MOLECULAR WEIGHT DETERMINATION FOR GASES FLOWING THROUGH THE COMPRESSOR

This application claims the benefit of Provisional Application No. 60/213,233, filed Jun. 20, 2000.

BACKGROUND OF THE INVENTION

1. Field of Invention

The present invention relates to a method and apparatus for the indirect determination of molecular weight of gases and their mixtures flowing through the axial or centrifugal compressor based on usage of compressor dynamics. This method is applicable to process controls, compressor controls, and real time analytical data acquisition, where the compressor is used for gas processing.

2. Background

A compressor is a type of rotating equipment commonly used for transfering energy to a flowing gas. The relationship between energy added to the gas, or head, and gas actual volumetric flow represents a measure of a compressor's performance. Every compressor manufacturer provides a tested map for head and flow parameters as part of the compressor's specification. Both parameters are multivariable functions of the initial measurable variables, such as pressure and temperature. The performance map reflects a relationship between head and flow by plotting those calculated variables and holding all other non-measurable parameters of the thermodynamic process constant.

A molecular weight measurement is very important to many chemical processes as well as for compressor control and surge protection. The industry uses special chromatography equipment or gas analyzers for these purposes. Most of these methods are very costly and have a significant time delay of output data, which reduces their efficiency and usefulness for process control.

SUMMARY OF THE INVENTION

An object of the present invention comprises providing a method of determining the molecular weight of a compressor gas by comparing the ratio of imaginary compressor map conditions and actual compressor operating conditions.

These and other objects of the present invention will become apparent to those skilled in the art upon reference to the following specification, drawings, and claims.

The present invention intends to overcome the difficulties encountered heretofore. To that end, a compressor for processing a compressor gas is provided. A performance map is provided that comprises a plurality of performance curves showing head and flow conditions at various compressor speeds. The performance curves terminate at one end at surge points. Also provided is a processing and calculating unit interfaced with the compressor, for measuring performance parameters of the compressor necessary to determine actual head and flow conditions of the compressor at a given processor speed and for performing calculations. The compressor map performance curves are converted into deviation curves, where the deviation curves represent deviations from the surge point at the head and flow conditions. The deviation curves are merged into a universal compressor curve with a merge-function to within a pre-defined tolerance. Imaginary map head and flow values are calculated using the universal compressor curve, merge-function, deviation curves, and performance curves at the compressor speed. A ratio of the imaginary map head and flow values is compared to a ratio of the actual head and flow values at the compressor speed to determine if the ratios are within a pre-defined tolerance of each other. If the ratios are not within the tolerance, then the imaginary head and flow map values are recalculated by varying either said imaginary head or flow parameters and the comparison is repeated until the ratios are within the pre-defined tolerance. The molecular weight of the compressor gas is calculated using a function of the actual and imaginary flow values and/or head values.

DISCLOSURE OF THE INVENTION

Figure 1:
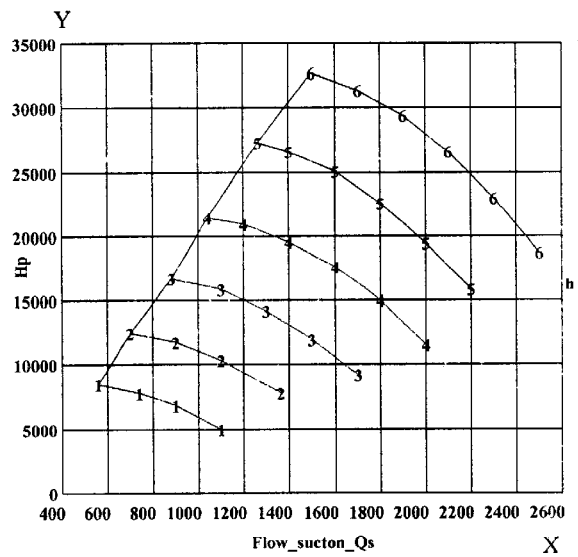
FIG. 1 is a compressor map sample for head and flow performance curves at different speeds.

The proposed method provides real time information using a molecular weight computation algorithm. This method is helpful when process gas molecular weight may change due to process requirements, gas mixture composition, or other process circumstances.

This algorithm performs cross-referenced flow and head calculations between an operating point at actual conditions and a reference point at map conditions. The relationship between the operating and reference points is invariant to the molecular weight. Using the following technique, it is possible to convert a multi-dimensional compressor map into a two-dimensional mathematical function, called a "universal compressor curve". This technique consequently allows one to use an actual process condition for the backward calculation to equivalent map conditions. The compressor map is used as a reference for actual process conditions and helps to calculate imaginary parameters at map conditions. Then, calculating an imaginary flow and head at map conditions, with respect to the map, and comparing those imaginary values with an actual flow and head in term of respective transmitter readings and an unknown actual molecular weight, the actual value of molecular weight can be easily obtained.

The method of algorithm construction provides low methodological error, decreasing toward the surge conditions up to theoretical zero. A computer simulation shows that the error may not exceed 3%. An operational margin is usually designed to exceed anticipated critical conditions far enough in advance to allow this method to detect the tendency of molecular weight change and recommend an appropriate correction action to the operator. Another advantage of the proposed method is that normally, no new hardware or additional wiring is required. Presently, most compressors and their control systems already have all necessary data to use this method. The proposed method utilizes an algorithmic measurement interacting between actual and equivalent map conditions.

For the orifice type meter, the actual volumetric flow through the compressor suction (inlet) calculated as $$(Qs)^2 = A^2 \cdot \frac{\Delta P_o}{\rho_s} = A^2 \cdot \frac{\Delta P_o * Z_s * R_o * (Tabs)_s}{MW * (Pabs)_s}, \text{ where:}$$

Qs-Suction (inlet) volumetric flow, Zs-Gas compressibility at suction conditions,
A-Orifice constant, Ro-Universal gas constant,
$\rho_s$-Gas density at inlet conditions, (Pabs)s-Absolute suction pressure,
MW-Molecular weight (Tabs)s-Absolute suction temperature.
$\Delta P_0$=Pressure differential cross flow measuring device (orifice)
Considering, that orifice sizing based on compressor map maximum volumetric flow through the machine inlet at the map conditions would be, then:

$$Q^2_{s\_max} = A^2 \cdot \frac{\Delta P_{o\_span}}{\rho_{s\_map}} = A^2 \cdot \frac{\Delta P_{o\_span} \cdot Z_{s\_map} \cdot R_o \cdot (Tabs)_{s\_map}}{MW_{map} \cdot (Pabs)_{s\_map}}, \quad (1)$$

Then designating:

$$K_{ZMW} = \frac{Z_s}{Z_{s\_map}} \cdot \frac{MW_{map}}{MW},$$

deriving for dimensionless flow parameter:

$$q_s^2 = \left(\frac{Q_s}{Q_{s\_max}}\right)^2 = K_{ZMW} \cdot \frac{(Tabs)_s}{(Tabs)_{s\_map}} \cdot \frac{(Pabs)_{s\_map}}{(Pabs)_s} \cdot \frac{\Delta P_o}{\Delta P_{o\_span}} \quad (2)$$

The polytropic head Hp for gases:

$$H_p = \frac{Zav \cdot Ro \cdot (Tabs)_s}{MW} \cdot \frac{(R_c^\sigma - 1)}{\sigma}, \text{ where:} \quad (3)$$

$R_c$=(Pabs)$_d$/(Pabs)$_s$-Compressor ratio, $\sigma$=(k−1)/(k·$\eta_p$)=($n_p$−1)/$n_p$=ln$T_c$/ln$R_c$−
$T_c$=(Tabs)$_d$/(Tabs)$_s$-Temperature ratio, Function of polytropic exponent $n_p$,
$R_o$—Universal gas constant, $\eta_p$-Compressor polytropic efficiency,
R=$R_o$/MW—Individual gas constant, k—Specific heat ratio for gases, $Z_{av}$=0.5·($Z_s$+$Z_d$)—Average compressibility.
$\Delta P_{o\_span}$=flow transmitter span (range)
The formula for polytropic head can be referenced to the constant part of this expression as $$H_{p\_scale} = \frac{Z_{s\_map} \cdot Ro \cdot (Tabs)_{s\_map}}{MW_{map}},$$

and considering that this part has the same dimension as polytropic head, then the dimensionless polytropic head would be:

$$h = \frac{Hp}{H_{p\_scale}} = K_{ZMW} \cdot \frac{(Tabs)_s}{(Tabs)_{s\_map}} \cdot \frac{(R_c^\sigma - 1)}{\sigma}. \quad (4)$$

Thus, the dimensionless head and flow for the conditions different from the map can be defined as:

$$q_s^2 = K_{ZMW} \cdot \frac{(Tabs)_s}{(Tabs)_{s\_map}} \cdot \frac{(Pabs)_{s\_map}}{(Pabs)_s} \cdot \frac{\Delta P_o}{\Delta P_{o\_span}} \quad (5)$$

$$h = K_{ZMW} \cdot \frac{(Tabs)_s}{(Tabs)_{s\_map}} \cdot \frac{(R_c^\sigma - 1)}{\sigma}$$

$$= K_{ZMW} \cdot \frac{(Tabs)_s}{(Tabs)_{s\_map}} \cdot \frac{1}{2} \cdot (T_c + 1) \cdot \ln R_c$$

For the map conditions, the following will be true $$K_{ZMW} = 1; \frac{(Tabs)_s}{(Tabs)_{s\_map}} = 1; \frac{(Pabs)_{s\_map}}{(Pabs)_s} = 1, \text{ then} \quad (6)$$

$$q^2_{s\_map} = \frac{\Delta P_{o\_map}}{\Delta P_{o\_span}} \text{ and}$$

$$h_{map} = \frac{\left(R_{c\_map}^{\sigma map} - 1\right)}{\sigma_{map}} = \frac{1}{2} \cdot (T_{c\_map} + 1) \cdot \ln R_{c\_map}$$

From the expressions (5) and (6) the head-to-flow-squared ratio for both, map and process conditions can be written as follows:

$$\frac{h_{map}}{q^2_{s\_map}} = \frac{\frac{\left(R_{c\_map}^{\sigma map} - 1\right)}{\sigma_{map}}}{\left(\frac{\Delta P_{o\_map}}{\Delta P_{o\_span}}\right)}, \quad (7)$$

$$\frac{h}{q_s^2} = \frac{\frac{(R_c^\sigma - 1)}{\sigma}}{\frac{(Pabs)_{s\_map}}{(Pabs)_s} \cdot \left(\frac{\Delta P_o}{\Delta P_{o\_span}}\right)} \quad (8)$$

The turbomachinery theory constitutes, that for similar operating points but different gases, the head-to-flow-squared ratio, inlet volume capacity, and polytropic work coefficient $\mu$P should be the same:

$$\frac{h_{gas1}}{q^2_{s\_gas1}} = \frac{h_{gas2}}{q^2_{s\_gas2}}; \frac{q_{s\_gas1}}{N_{gas1}} = \frac{q_{s\_gas2}}{N_{gas2}}; \mu_{p\_gas1} = \mu_{p\_gas2} \text{ or } \frac{h_{gas1}}{N^2_{gas1}} = \frac{h_{gas2}}{N^2_{gas2}}.$$

From these basic statements, the definition of a reference point between map and actual conditions can be derived as the point where: for the same speed and head-to-flow-squired ratio—the volumetric flow and head should be also the same:

$$\frac{h_{map}}{q^2_{s\_map}} = \frac{h}{q_s^2} \text{ and for } N = N_{map}, \text{ then } h_{map} = h, q^2_{s\_map} = q_s^2 \quad (9)$$

The relationship (9) serves as interactive bridge between map and actual parameters to calculate a molecular weight from the incoming process variables:

1. From flow, pressure and temperature signals, the system calculates an operating head-to-flow-squared ratio for actual conditions as per expression (8);
2. Then, for an actual speed and head-to-flow-squared ratio, the system determines the reference point on the map with the same ratio of pair values of $h_{map}$ and $q_{s\_map}^2$ in accordance to (9);

3. Using (5), (6) and (9) the following relationships can be derived between a reference point at map conditions and an actual point at operating conditions:

$$q_{s\_map}^2 = \frac{\Delta P_{o\_map}}{\Delta P_{o\_span}} = q_s^2 = \frac{Z_s}{Z_{s\_map}} \cdot \frac{MW_{map}}{MW} \cdot$$

$$\frac{(Tabs)_s}{(Tabs)_{s\_map}} \cdot \frac{(Pabs)_{s\_map}}{(Pabs)_s} \cdot \frac{\Delta P_o}{P_{o\_span}}$$

$$h_{map} = \frac{(R_{c\_map}^{\sigma_{map}} - 1)}{\sigma_{map}} = h = \frac{Z_s}{Z_{s\_map}} \cdot \frac{MW_{map}}{MW} \cdot$$

$$\frac{(Tabs)_s}{(Tabs)_{s\_map}} \cdot \frac{(R_c^\sigma - 1)}{\sigma}$$

Considering that compressibility Z can be assumed constant as per common practice, then from the above relationships, the following two expressions can be derived for molecular weight calculations:

$$MW1 = MW_{map} \cdot \frac{(Tabs)_s}{(Tabs)_{s\_map}} \cdot \frac{(Pabs)_{s\_map}}{(Pabs)_s} \cdot \frac{\Delta P_o}{P_{o\_span}} \cdot \frac{1}{q_{s\_map}^2} \quad (10)$$

$$MW2 = MW_{map} \cdot \frac{(Tabs)_s}{(Tabs)_{s\_map}} \cdot \frac{\frac{(R_c^\sigma - 1)}{\sigma}}{h_{map}}$$

Either formula or the average of the two provides a sufficient result.

Figure 2:
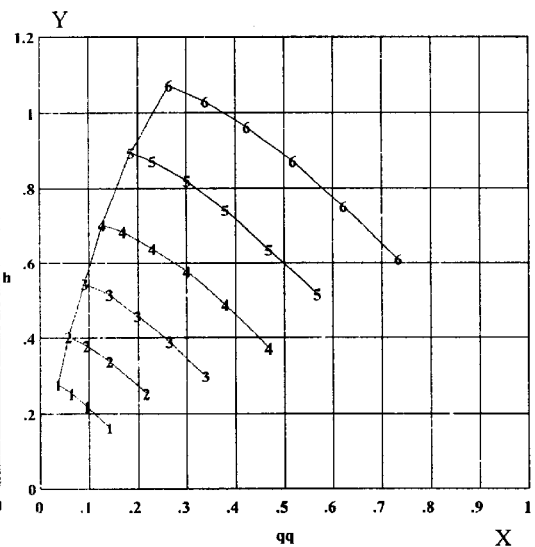
FIG. 2 is a compressor map recalculated for the dimensionless parameters, head and how, at different speeds.

Usually, the compressor's manufacturer provides a compressor performance map as shown in FIG. 1. This map can be converted into the dimensionless head and flow-squared map as depicted in FIG. 2. A surge limit line on the map can be described as a combination of two surge-functions of speed, such as polytropic head and flow-squared for respective surge points and speeds:

$$H_{p\_sg\_map} = F_{h\_map}^{sg}(N); \quad Q_{s\_sg\_map}^2 = F_{q\_map}^{sg}(N),$$

where flow is taken squared to simplify further transition to a pressure differential across the orifice ($Q^2 \sim q^2$). Consequently, for the dimensionless head and flow list-functions of speed:

$$h_{sg\_map} = f_{h\_map}^{sg}(N); \quad q_{s\_sg\_map}^2 = f_{q\_map}^{sg}(N).$$

Figure 3:
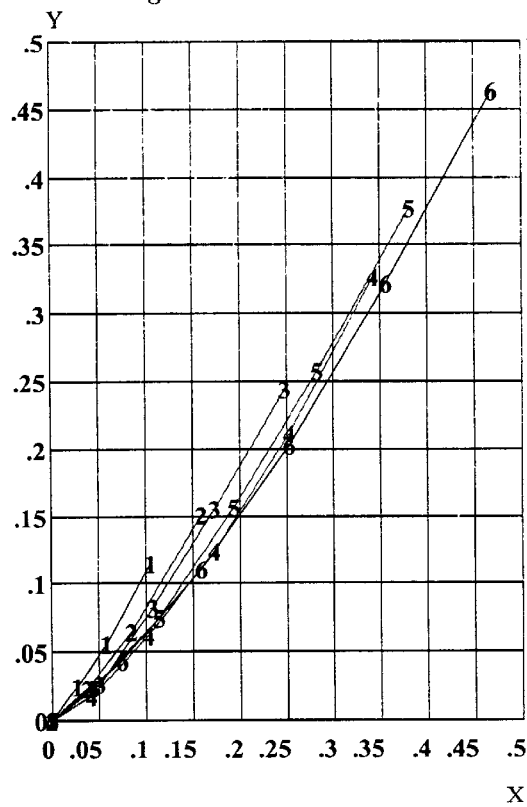
FIG. 3 is the graphic of head and flow deviations from their respective surge points for different speeds.
Figure 4:
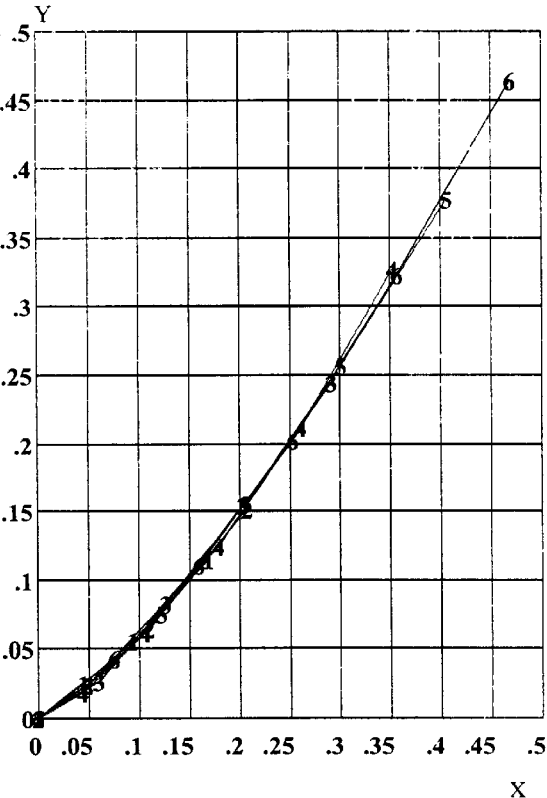
FIG. 4 is the graphic of head deviation as a single function of characterized flow deviation.

For each performance curve on the map, a respective deviations curve can be built, where the deviation variables are the distance between head and flow at operating points and their respective values at the surge points for the same speed:

$$\Delta h_{map} = f_{h\_map}^{sg}(N) - h_{map}|^N$$

$$\Delta q_{s\_map} = q_{s\_map}^2|^N - f_{q\_map}^{sg}(N),$$

where $q_{s\_sg\_map}^2 \leq q_{s\_map}^2 \leq q_{s\_map\_max}^2$, $h_{map\_min} \leq h_{map} \leq h_{map\_sg}$, and $q_{s_{map}}^2|^N$ and $h_{map}|^N$—are flow-squared and head at map conditions for the specified speed. These values, in the respective coordinate system forming the curve specter for the different speeds. These curves originate at the coordinate point of origin and represent the appropriate map performance curves. The graphic of these curves is presented on FIG. 3, where the vertical axis is $\Delta h_{map}$ and the horizontal axis is $\Delta q_{s\_map}$. If an appropriate speed characterizer f(N), a so called "merge-function", is applied to either the $\Delta q$ or the $\Delta h$ parameter, with reference to flow, then:

$$\Delta h_{map}(N) = f_{h\_map}^{sg}(N) - h_{map}|^N \quad (11)$$

$$\Delta q_{s\_map} = f(N, \Delta q_{s\_map}),$$

and the curves on FIG. 3 merge into the one common curve, called a "universal compressor curve" $F_{ucc}$ as it shown on FIG. 4. This curve can be extrapolated into the two-dimensional, speed irrelevant, single argument function between characterized and non-characterized parameters of head and flow-squared deviations from their respective surge points such as:

$$\Delta h_{map} = F_{ucc}(\Delta q_{c\_map})$$

Substituting those parameters by their respective expressions in (11) for a specified speed N $$f_{h\_map}^{sg}(N) - h_{map}|^{N-F}{}_{ucc}(f\{N, [q_{s\_map}^2]^{N-f}q{-}_{map}^{sg}(N)]\})$$

Then, head and flow at map conditions can be described as an explicit function within a function for each N=N_actual:

$$h_{map}|^N = f_{h\_map}^{sg}(N) - F_{ucc}\langle f\{N, [q_{s\_map}^2|^N - f_{q\_map}^{sg}(N)]\}\rangle \quad (12)$$

$$\frac{h_{map}|^N}{q_{s\_map}^2|^N} - \frac{(h|)^N}{(q_s^2|)^N} = 0 (\text{or less then predetermind error})$$

The relationship (12) presents two equations with two unknown parameters $h_{map}|^N$ and $q_{s\_map}^2|^N$. These two equations can be resolved using a simple iterative technique that for the any given actual speed and head-to-flow-squared ratio returns only one pair of head and flow map-parameters which represent a reference point at map conditions and have the same $h_{map}/q_{s\_map}^2$ ratio for the given speed. This reference point represents what the flow and head would be at map conditions (so called imaginary parameters). Once the flow and head at map conditions are known, then from (10) the molecular weight can be obtained.

BEST MODE OF IMPLEMENTING THE INVENTION

For practical application, the final algorithm has to be transformed into the process signals developed from field transmitters $$MW1 = \frac{MW_{map} \cdot T_{scale}}{(Tabs)_{s\_map}} \cdot \frac{(Pabs)_{s\_map}}{P_{scale}} \cdot \frac{\Delta P_{o\_span}}{\Delta P_{o\_map}} \cdot$$

$$\Delta P_{o\_sv} \cdot \frac{T_{s\_sv} \cdot G_{st} + B_t}{P_{s\_sv} \cdot G_{sp} + B_p} =$$

$$= \frac{MW_{map} \cdot T_{scale}}{2 \cdot (Tabs)_{s\_map}} \cdot \frac{2 \cdot (Pabs)_{s\_map}}{P_{scale}} \cdot \frac{\Delta P_{o\_sv}}{q_{s\_map}^2} \cdot \frac{T_{s\_pv}}{P_{s\_pv}} =$$

$$= K \cdot K1 \cdot \frac{\Delta P_{o\_sv}}{q_{s\_map}^2} \cdot \frac{T_{s\_pv}}{P_{s\_pv}}$$

$$MW2 = \frac{MW_{map} \cdot (Tabs)_s \cdot (T_c + 1) \cdot \ln R_c}{2 \cdot (Tabs)_{s\_map} \cdot h_{map}}$$

$$= \frac{MW_{map} \cdot T_{scale}}{2 \cdot (Tabs)_{s\_map}} \cdot \frac{(T_{d\_pv} + T_{s\_pv}) \cdot \ln\left(\frac{P_{d\_pv}}{P_{s\_pv}}\right)}{h_{map}} =$$

-continued $$= K \cdot \frac{(T_{d\_pv} + T_{s\_pv}) \cdot \ln\left(\frac{P_{d\_pv}}{P_{s\_pv}}\right)}{h_{map}}$$

$$\text{where: } K = \frac{MW_{map} \cdot T_{scale}}{2 \cdot (Tabs)_{s\_map}}; \quad K1 = \frac{2 \cdot (Pabs)_{s\_map}}{P_{scale}},$$

and subscripts "pv" and "sv" refer to process signal variable and transmitter signal variable, which relate to each other as per following conversion rule:

$$(Aabs) =$$

$$Ascale \cdot \left(\frac{A}{Ascale} + \frac{Aoffset}{Ascale}\right) = Ascale \cdot \left[\frac{A}{Aspan} * \frac{Aspan}{Ascale} + \frac{Aoffset}{Ascale}\right] =$$

$$= Ascale \cdot [A_{\_sv} \cdot Gain + Bias] = Ascale \cdot A_{\_pv}$$

The final expression for average MW calculation:

$$MW = \frac{MW1 + MW2}{2} = \tag{13}$$

$$\frac{K}{2} \cdot \left[K1 \cdot \frac{\Delta P_{o\_sv}}{q_{s\_map}^2} \cdot \frac{T_{s\_pv}}{P_{s\_pv}} + \frac{(T_{d\_pv} + T_{s\_pv}) \cdot \ln\left(\frac{P_{d\_pv}}{P_{s\_pv}}\right)}{h_{map}}\right]$$

Figure 5:
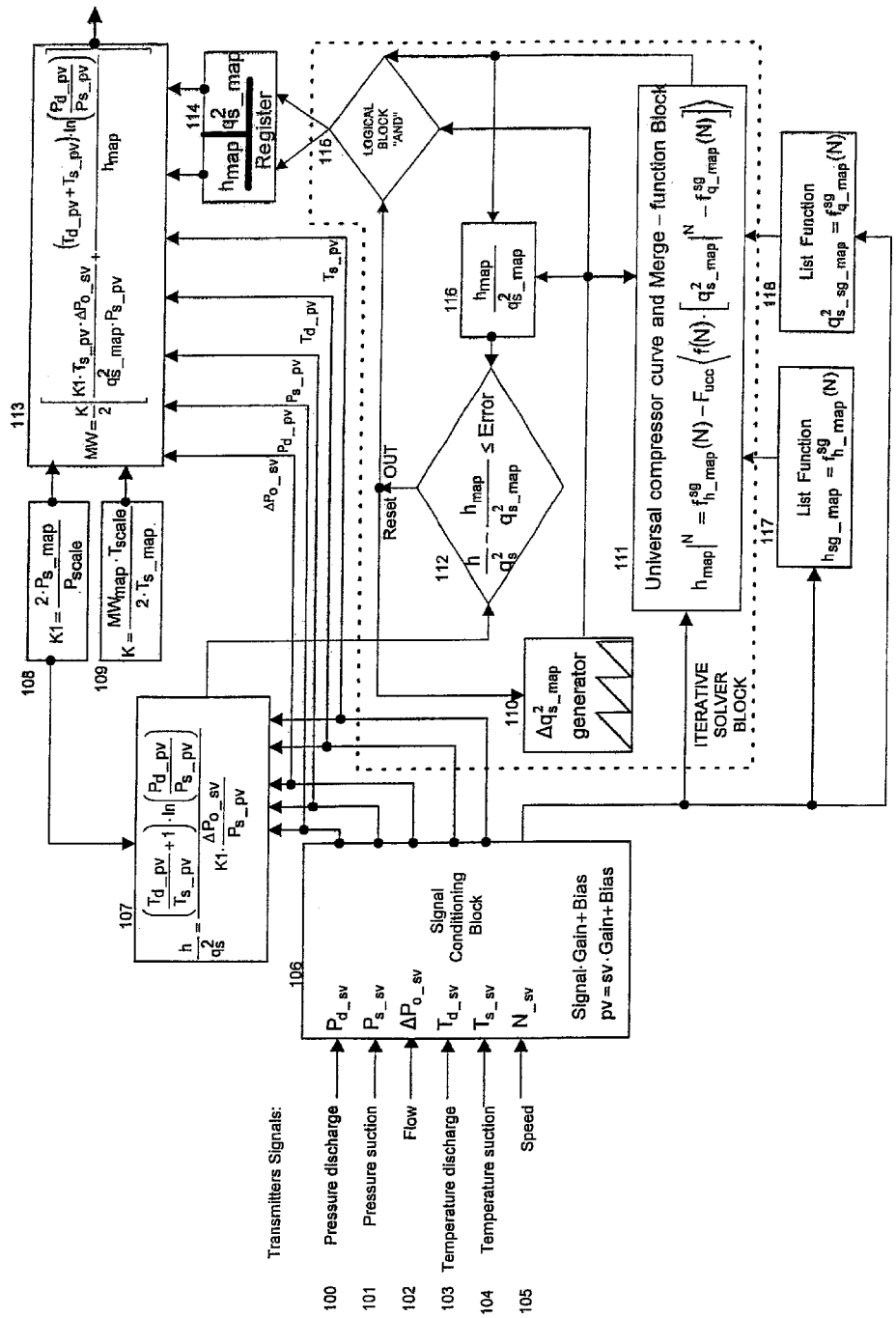
FIG. 5 is the block diagram of the computation device algorithm.

The following functions must be defined from the compressor map:

$f_{q\_map}{}^{sg}(N_{sv})$—flow surge-function of speed transmitter signal, module 118 in FIG. 5;

$f_{h\_map}{}^{sg}(N_{sv})$—head surge-function of speed, module 117 in FIG. 5;

$f(N_{sv})$—merging characterizer of flow or head deviations curves as a function of speed, module 111 in FIG. 5;

$\Delta h_{map} = F_{ucc}(\Delta q_{c\_map})$—Extrapolated universal compressor curve as a list-function of head and characterized flow-squared deviations from respective surge points, module 111 in FIG. 5.

The relationship between actual head and volumetric flow-squared, $h/q_s^2$, can be calculated using the signals from suction and discharge pressure and temperature transmitters, plus DP-flow transmitter and speed. Those signals are represented on FIG. 5 under #100–105. Module 106 provides input signal conditioning and module 107 is calculating $h/q_s^2$ ratio. The imaginary head and flow-squared values at map conditions for the given speed $h_{map}|^{Nsv}$ and $q_{s\_map}{}^2|^{Nsv}$ can be computed from the expression (12) using an iterative calculation program technique (Iterative Solver Block). As soon as the error falls below a predetermined value, the Iterative Solver generates two output values of head and flow-squared at imaginary map conditions that the logic block writes into the respective register 114, then the system repeats a calculating cycle. The outputs from modules 114, 108, 109 and 106 are used by module 113 to calculate an actual molecular weight MW. The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclosure before them will be able to make modifications and variations therein without departing from the scope of the invention.

What is claimed is:

1. A method of determining a molecular weight of a compressor gas by comparing the ratio of imaginary compressor map conditions and actual compressor operating conditions, said method comprising:

providing a compressor for processing a compressor gas;

providing a compressor map with a plurality of performance curves showing head and flow conditions at various compressor speeds wherein said curves terminate at one end at surge points;

providing a processing and calculating unit interfaced with said compressor, for measuring performance parameters of said compressor necessary to determine actual head and flow conditions of said compressor at a given compressor speed and for performing calculations;

converting said compressor map performance curves into deviation curves, wherein said deviation curves represent deviations from said surge points at said head and flow conditions;

merging said deviation curves into a universal compressor curve with a merge-function to within a pre-defined tolerance;

calculating an imaginary map head and flow values using said universal compressor curve, merge-function, deviation curves, and performance curves at said compressor speed;

comparing a ratio of said imaginary map head and flow values to a ratio of said actual head and flow values at said compressor speed to determine if said ratios are within a pre-defined tolerance of each other;

if said ratios are not within said tolerance, then recalculating said imaginary head and flow map values by varying either said imaginary head or flow values and repeating said comparison until said ratios are within said pre-defined tolerance; and calculating the molecular weight of said compressor gas by using a function of said actual and imaginary flow values.

2. The invention in accordance with claim 1 wherein said molecular weight of said compressor gas is calculated using a function of said actual and imaginary head values, instead of using said flow.

3. The invention in accordance with claim 1 wherein said molecular weight of said compressor gas is calculated by taking an average of two molecular weight calculations wherein one molecular weight is calculated by using a function of said actual and imaginary head, and a second molecular weight is calculated by using a function of said actual and imaginary flow measurements squared.

4. The invention in accordance with claim 1 wherein said performance parameters comprise pressure discharge, pressure suction, flow, temperature discharge, temperature discharge, and temperature suction.

5. The invention in accordance with claim 1 wherein said method of determining molecular weight is continuous and real-time.

6. An apparatus for determining a molecular weight of a compressor gas by comparing the ratio of imaginary compressor map conditions and actual compressor operating conditions, said method comprising:

a compressor for processing a compressor gas;

a compressor map with a plurality of performance curves showing head and flow conditions at various compressor speeds wherein said curves terminate at one end at surge points;

a processing and calculating unit interfaced with said compressor, for measuring performance parameters of said compressor necessary to determine actual head and flow conditions of said compressor at a given compressor speed and for performing calculations;

means for converting said compressor map performance curves into deviation curves, wherein said deviation curves represent deviations from said surge points at said head and flow conditions;

means for merging said deviation curves into a universal compressor curve with a merge-function to within a pre-defined tolerance;

calculating an imaginary map head and flow values using said universal compressor curve, merge-function, deviation curves, and performance curves at said compressor speed;

means for comparing a ratio of said imaginary map head and flow values to a ratio of said actual head and flow values at said compressor speed to determine if said ratios are within a pre-defined tolerance of each other;

if said ratios are not within said tolerance, then means for recalculating said imaginary head and flow map values by varying either said imaginary head or flow values and repeating said comparison until said ratios are within said pre-defined tolerance; and means for calculating the molecular weight of said compressor gas by using a function of said actual and imaginary flow values.

* * * * *